United States Patent
Kanou et al.

(10) Patent No.: US 9,181,569 B2
(45) Date of Patent: Nov. 10, 2015

(54) METHOD FOR PRODUCING ACRYLAMIDE

(75) Inventors: Makoto Kanou, Yokohama (JP); Kiyonobu Niwa, Yokohama (JP)

(73) Assignee: Mitsubishi Rayon co., Ltd., Tokyo (JP)

( * ) Notice: Subject to any disclaimer, the term of this patent is extended or adjusted under 35 U.S.C. 154(b) by 0 days.

(21) Appl. No.: 14/122,052

(22) PCT Filed: May 29, 2012

(86) PCT No.: PCT/JP2012/063728
§ 371 (c)(1),
(2), (4) Date: Nov. 25, 2013

(87) PCT Pub. No.: WO2012/165415
PCT Pub. Date: Dec. 6, 2012

(65) Prior Publication Data
US 2014/0134683 A1    May 15, 2014

(30) Foreign Application Priority Data

May 31, 2011  (JP) ................................. 2011-121849

(51) Int. Cl.
*C07C 231/06* (2006.01)
*C07C 233/09* (2006.01)
*C12P 13/02* (2006.01)

(52) U.S. Cl.
CPC ............. *C12P 13/02* (2013.01); *C07C 231/06* (2013.01)

(58) Field of Classification Search
USPC .......................................... 564/128; 558/462
See application file for complete search history.

(56) References Cited

U.S. PATENT DOCUMENTS

| | | | |
|---|---|---|---|
| 4,248,968 A * | 2/1981 | Watanabe et al. | ............. 435/129 |
| 4,414,331 A | 11/1983 | Watanabe et al. | |
| 9,057,084 B2 * | 6/2015 | Kanou et al. | ................... 558/462 |
| 2004/0175809 A1 | 9/2004 | Peterson et al. | |
| 2004/0219647 A1 | 11/2004 | Murao et al. | |
| 2011/0021819 A1 * | 1/2011 | Kanou et al. | ................... 564/126 |
| 2011/0171701 A1 * | 7/2011 | Kano et al. | .................... 435/129 |

FOREIGN PATENT DOCUMENTS

| | | | |
|---|---|---|---|
| EP | 2336346 A1 * | 6/2011 | |
| JP | 6 179630 | 6/1994 | |
| JP | 2001 340091 | 12/2001 | |
| JP | 2004 524047 | 8/2004 | |
| WO | 03 000914 | 1/2003 | |
| WO | WO 2009113654 A1 * | 9/2009 | |
| WO | 2010 038832 | 4/2010 | |
| WO | WO 2010038832 A1 * | 4/2010 | |

OTHER PUBLICATIONS

International Search Report Issued Jul. 3, 2012 in PCT/JP12/063728 Filed May 29, 2012.

The Extended European Search Report issued Oct. 27, 2014, in Application No. / Patent No. 12794114.4-1501 / 2716765.

* cited by examiner

*Primary Examiner* — Nyeemah A Grazier

(74) *Attorney, Agent, or Firm* — Oblon, McClelland, Maier & Neustadt, L.L.P.

(57) ABSTRACT

The present invention relates to a method for producing acrylamide comprising: supplying a raw material water to a reactor, supplying acrylonitrile to the reactor, and hydrating acrylonitrile using a biocatalyst, wherein a temperature of the raw material water in the supplying step of the raw material water to the reactor is equal to or more than freezing point of the raw material water and lower than the reaction temperature by 5° C. or more. The present invention can be provided to the method of producing acrylamide which can be removed the reaction heat produced at the hydration reaction of acrylonitrile effectively with a low cost.

13 Claims, No Drawings

METHOD FOR PRODUCING ACRYLAMIDE

TECHNICAL FIELD

The present invention relates to a method for producing acrylamide from acrylonitrile using a biocatalyst. The present invention claims priority on the basis of Japanese Patent Application No. 2011-121849 filed in Japan on May 31, 2011, the contents of which are incorporated herein by reference.

BACKGROUND ART

The producing method of an objective compound by using a biocatalyst is used for producing many compounds, because it has some advantages, for example, reaction conditions are mild, a product having a high purity can be obtained since an amount of by-product is small, and a production process can be simplified. For example, in the case of production of an amide compound such as acrylamide, since nitrile hydratase, which is an enzyme for converting a nitrile compound such as acrylonitrile into an amide compound, was found, biocatalysts including the enzyme have been widely used.

In the case of producing acrylamide using the biocatalyst, it is necessary to remove a reaction heat. In general, the biocatalyst is easily deactivated with heat. A reaction which converts the acrylonitrile to acrylamide is an exothermic reaction, and a temperature of a reaction solution rises by the reaction heat. If the reaction heat is not sufficiently removed, the biocatalyst is deactivated by the heat.

The method for removing the reaction heat, for example, a method of cooling with a heat exchanger by circulating a portion of a reaction mixture to a pump circulation passage, using a reactor comprising the pump circulation passage which provided with the heat exchanger (Patent Document 1), a method of using a plug flow type reactor which is a double pipe type or a shell and tube type (Patent Document 2), and a method which is providing a jacket or cooling coil to a reaction tank (Patent Document 3), has been known.

PRIOR ART DOCUMENT

Patent Document

Patent Document 1: Japanese Unexamined Patent Publication (Translation of PCT Application) No. 2004-524047
Patent Document 2: Japanese Unexamined Patent Publication No. 2001-340091
Patent Document 3: International Publication WO 03/00914

SUMMARY OF THE INVENTION

Problem to be Solved by the Invention

In order to industrially utilize the method for producing acrylamide using the biocatalyst, it is important to produce acrylamide at low cost and with efficiency. However, in the conventional method, it is difficult to produce acrylamide at low cost.

For example, as described above, when the removal of the reaction heat is insufficient, the amount of the catalyst used for producing acrylamide is increased because the biocatalyst is deactivated by the reaction heat. As a result, the cost of the catalyst increases, and thereby increases the producing cost of acrylamide compound. On the other hand, in the case of removing the reaction heat sufficiently by the method disclosed in Patent Documents 1 to 3, the facility cost or the energy cost is increased.

For example, in the method of providing the pump circulation passage which provided with the heat exchanger to the exterior portion of the reactor disclosed in Patent Document 1, facility cost is increased because the apparatus becomes complicated. Also, a great deal of energy is expended for circulating the reaction solution to the heat exchanger at the exterior portion of the reactor, and therefore, producing cost is increased.

Also, if the productivity per reactor is increased, an oversize heat exchanger is required. As a result, facility cost is increased.

In the methods according to Patent Documents 2 to 3, since it takes time to remove heat, removal of the reaction heat of the immediately after the reaction tends to be insufficient. Examples of removing heat methods in a short time includes the method that is decreased the temperature of a cooling water excessively. For example, Patent Document 3 discloses the method using the cooling water having a lower temperature of about 5 to 15° C. than the reaction temperature to maintain a constant level of the temperature of the reaction tank. However, in the case of reacting at a lower temperature, since it is necessary to set the temperature of the cooling water low according to the reaction temperature, energy cost is increased. Further, when the temperature of the cooling water is excessively lowered, there is concern that the acrylamide crystal is formed on the cooling surface. In this case, by forming the crystal on the cooling surface, the removal of the reaction heat is not insufficient, but a problem of blocking of the pipe also occurs. As a result, maintenance and the like become necessary.

The present invention is made in view of the above matter, and its object is to provide a method for producing acrylamide by hydrating acrylonitrile using the biocatalyst, wherein the reaction heat at the time of hydration of acrylonitrile can be efficiently removed at a low cost.

Means for Solving the Problems

Conventionally, in the method for producing acrylamide using the biocatalyst, a raw material water used for the hydration of the acrylonitrile is adjusted to the same temperature as the reaction temperature after supplied to the reactor (for example, according to Patent Document 1) . However as a result of diligent studies to solve the above problem, the present inventors found that when the reaction temperature when hydrating acrylonitrile is 10 to 40° C., the reaction heat at the time of hydrating the acrylonitrile can be efficiently removed by supplying the raw material water to the reactor after adjusting it to a temperature equal to or more than freezing point and lower than the reaction temperature by 5° C. or more.

The present invention comprises the below aspects.

[1] A method for producing acrylamide by supplying acrylonitrile and a raw material water to a reactor and hydrating acrylonitrile using a biocatalyst, wherein a temperature of the raw material water supplied to the reactor is equal to or more than freezing point and lower than a reaction temperature by 5° C. or more.

[2] The method for producing acrylamide according to [1], wherein the temperature of acrylonitrile supplied to the reactor is equal to or more than freezing point of the raw material water and lower than the reaction temperature by 5° C. or more.

[3] The method for producing acrylamide according to [1] or [2], wherein hydration reaction of acrylonitrile is performed by a semi batch reaction or a continuous reaction.

Further, the present invention comprises the below aspects.

[1] A method for producing acrylamide comprising: supplying a raw material water to a reactor, supplying acrylonitrile to the reactor, and hydrating acrylonitrile using a biocatalyst, wherein a temperature of the raw material water in supplying the raw material water to the reactor is equal to or more than freezing point of the raw material water and lower than the reaction temperature by 5° C. or more;

[2] the method for producing acrylamide according to [1], wherein a temperature of acrylonitrile in supplying acrylonitrile to the reactor is equal to or more than freezing point of the raw material water and lower than the reaction temperature by 5° C. or more; and

[3] the method for producing acrylamide according to [1] or [2], wherein in hydrating acrylonitrile using the biocatalyst, hydrating reaction of acrylonitrile is performed by a semi batch reaction or a continuous reaction.

Effect of the Invention

According to the present invention, in the method for producing acrylamide by hydrating acrylonitrile using the biocatalyst, since the reaction heat at the time of hydrating of acrylonitrile can be efficiently removed, the method for producing acrylamide at a low cost can be provided.

MODE(S) FOR CARRYING OUT THE INVENTION

Hereinafter, the method for producing acrylamide of the present invention is explained in detail below. The scope of the present invention is not limited to the description. In addition to the following examples, the present invention can be suitably changed and then practiced within a range in which the effects of the present invention are not reduced. In addition, all the publications such as prior art documents, Unexamined Patent Publication, patents and other patent documents cited herein are incorporated herein by reference.

In the producing method of the present invention, acrylamide is produced by supplying acrylonitrile and a raw material water to a reactor, and hydrating acrylonitrile using a biocatalyst. In other words, in the method for producing acrylamide of the present invention, it comprises that supplying the raw material water to the reactor, supplying acrylonitrile to the reactor, and hydrating acrylonitrile using the biocatalyst.

The raw material water is used for hydrating reaction with acrylonitrile when acrylamide is produced. Examples of the raw material water include water and aqueous solution such as acid and salt are dissolved in water. Examples of acid include phosphoric acid, acetic acid, citric acid, boric acid, acrylic acid, and formic acid. Examples of salt include sodium salt of the acid, potassic salt, and ammonium salt. Although it is not particularly limited, specific examples of the raw material water include pure water, city water, tris buffer, phosphoric acid buffer, acetic acid buffer, citric acid buffer, and boric acid buffer. It is preferable that the pH (20° C.) of the raw material water is 5 to 9.

In the producing method of the present invention, the temperature of the raw material water supplied to the reactor is equal to or more than freezing point (congeal point) of the raw material water and lower than the reaction temperature by 5° C. or more.

In the method for producing acrylamide of the present invention, it is characterized in that the temperature of the raw material water is equal to or more than freezing point (congeal point) of the raw material water and lower than the reaction temperature by 5° C. or more, preferably higher than freezing point and lower than the reaction temperature by 10° C. or more, and more preferably higher than freezing point and lower than the reaction temperature by 20° C. or more. As a result, the reaction heat generated due to the hydration of acrylonitrile is efficiently removed, and rise in the temperature of the reaction solution can be suppressed. Therefore, the deactivation of the biocatalyst is suppressed and the catalyst cost can be controlled. Further, when hydrating of acrylonitrile, cooling with the cooling water is conducted for controlling of the reaction temperature or removing heat. However, since the present invention can be cooled by using the raw material water at a predetermined temperature, it is not necessary to excessively lower the temperature of the cooling water, and energy cost can be reduced.

In other words, in the method for producing acrylonitrile of the present invention, it is preferable that the temperature of the cooling water is 3 to 15° C., and more preferable is lower 10 to 20° C. than the reaction temperature.

Also, since it is not necessary to excessively lower the temperature of the cooling water, problems that the crystal of the obtained acrylamide is formed, the cooling efficiency is decreased along with it, and pipe blockage tend not to occur.

Further, conversion efficiency from acrylonitrile to acrylamide increases.

On the other hand, when the temperature of the raw material water is lower than freezing point, the energy cost required the cooling of the raw material water does not increase, but the raw material water becomes easy to congeal. As a result, it becomes difficult to stably produce acrylamide.

When the value of the temperature of the raw material water subtracted from the reaction temperature is less than 5° C., that is, when the difference between the reaction temperature and the temperature of the raw material water is less than 5° C., removal of the reaction heat becomes insufficient.

When the temperature of the raw material water in the supplying step of the raw material water to the reactor is equal to or more than freezing point, and lower than the reaction temperature by 5° C. or more, since the removal of the reaction heat becomes sufficient and acrylamide can be stably produced, it is preferable. Also, the conversion efficiency from acrylonitrile to acrylamide decreases. The difference between the reaction temperature and the temperature of the raw material water (reaction temperature-temperature of the raw material water) is equal to or more than 5° C., preferably equal to or more than 10° C., and more preferably equal to or more than 20° C. The upper limit is not particularly limited as long as that the temperature of the raw material water does not become less than freezing point.

In the producing method of the present invention, further, it is preferable that the temperature of acrylonitrile supplied to the reactor is equal to or more than freezing point of the raw material water supplied to the reactor, and lower than the reaction temperature by 5° C. or more. As a result, the effect of the present invention further increases.

The difference between the reaction temperature and the temperature of acrylonitrile (reaction temperature-temperature of acrylonitrile) is preferably equal to or more than 5° C., and more preferably equal to or more than 10° C. The upper limit is not particularly limited as long as that the temperature of acrylonitrile does not become less than the freezing point of raw material water.

Examples of the biocatalyst include an animal cell, plant cell, organelle, bacterial cell of microorganism (living cell or dead cell), and treated products thereof, which contain an enzyme (nitrile hydratase) for catalyzing a purpose reaction.

Examples of the treated products include an enzyme (a crude enzyme or purified enzyme) extracted from an animal cell, plant cell, organelle, or bacterial cell of microorganism; or the animal cell, plant cell, organelle, bacterial cell of microorganism, or enzyme themselves immobilized to a carrier.

Examples of the immobilization method include an entrapping method, cross-linking method, and carrier binding method. The entrapping method is a method in which a bacterial cell or enzyme is enclosed with a fine lattice of polymer gel or coated with a semipermeable polymer membrane. The cross-linking method is a method in which an enzyme is cross-linked with a reagent having 2 or more functional groups (polyfunctional crosslinking agent). The carrier binding method is a method in which an enzyme is bound to a water-insoluble carrier.

Examples of carriers (immobilization carriers) to be used for immobilization include glass beads, silica gel, polyurethane, polyacrylamide, polyvinyl alcohol, carrageenan, arginic acid, agar and gelatin.

As for the biocatalyst, particularly, bacterial cell of microorganism or treated products thereof are preferable.

Examples of microorganisms include microorganisms belonging to *Nocardia, Corynebacterium, Bacillus, Pseudomonas, Micrococcus, Rhodococcus, Acinetobacter, Xanthobacter, Streptomyces, Rhizobium, Klebsiella, Enterobacter, Erwinia, Aeromonas, Citrobacter, Achromobacter, Agrobacterium*, and *Pseudonocardia*.

An example of treated product of the microorganisms includes nitrile hydratase produced by the microorganisms.

The amount of the biocatalyst to be used varies depending on the type and form of the biocatalyst to be used, but it is preferably adjusted so that the activity of the biocatalyst introduced within the reactor becomes about 50 to 500 U per 1 mg of dried cell at reaction temperature of 10° C. Where, the aforementioned U (unit) means producing 1 micromole of acrylamide from acrylonitrile in 1 minute, and it is a value measured by using acrylonitrile used in the producing.

Also, it is preferable that the amount of the raw material water to be used is adjusted so that concentration of acrylamide with respect to the total mass of the reaction mixture including acrylamide after the step of hydration is 25 to 60 mass %, more preferably 40 to 55 mass %. In other words, it is preferable that 186 to 448 kg of the raw material water is fed with respect to 1,000 kg of acrylonitrile.

Methods of hydrating acrylonitrile using the biocatalyst include a batch reaction, a semi batch reaction, and a continuous reaction, and any of the reaction can be applied. The batch reaction is a method in which the total amount of reaction raw materials (including the biocatalyst, acrylonitrile, and raw material water) are fed into the reactor and then a reaction is performed. The semi batch reaction is a method in which a part of reaction raw materials are fed into the reactor and then remaining reaction raw materials are fed continuously or intermittently and a reaction is performed. The continuous reaction is a method of continuous production by continuously or intermittently supplying reaction raw materials and continuously or intermittently taking out the reaction mixture (including reaction raw materials and acrylamide produced) from the reactor, without taking out the total amount of the reaction mixture in the reactor. Since it is industrially easy to produce a large amount of acrylamide efficiently, the semi batch reaction or the continuous reaction is preferred.

As the form of the reactor, reactors of various forms such as stirred-tank type, fixed-bed type, fluidized-bed type, moving-bed type, column type, and tubular type can be used.

One reactor or a plurality of reactors may be used. When plurality of reactors are used in parallel, acrylamide concentration of the reaction mixture in the reactor positioned more downstream side becomes higher. In other words, acrylamide concentration of the side in which the catalyst is taken away from the reaction system is higher. Therefore, acrylamide concentration of the acrylamide aqueous solution which finally obtained can be adjusted depending on the number of reactors.

To explain in detail, when reaction is performed continuously using a plurality of reactors, it is necessary to connect the plurality of reactors in series, supply the biocatalyst, acrylonitrile, and the raw material water continuously to the upstream reactor, and take out the reaction mixture continuously from the downstream reactor. In this way, in the method of connecting the plurality of reactors and performing continuous reaction, the conversion ratio to acrylamide becomes higher in the downstream side reactor, and acrylamide concentration of the reaction mixture becomes high. Also, in the reaction method where the plurality of reactors is used, since acrylamide concentration of the reaction mixture differs in each reactor, the reaction mixture with purpose acrylamide concentration can be obtained without largely changing the reaction condition.

When reaction is performed continuously using the plurality of reactors, the reactor to which the biocatalyst and acrylonitrile are introduced is not limited only to the reactor positioned in the most upstream, but can be introduced to the reactor in its downstream, to the extent that it is not too deteriorated the reaction efficiency and like so.

Although the reaction temperature (reaction mixture temperature) of hydration of acrylonitrile is not limited, it is preferably 10 to 50° C., more preferably 20 to 40° C., and most preferably 15 to 25° C. When the reaction temperature is 10° C. or higher, the reaction activity of the biocatalyst can be sufficiently increased. Also, when the reaction temperature is 40° C. or lower, it becomes easier to suppress deactivation of the biocatalyst. Although the reaction time is not limited, but is preferably 1 to 50 hours, and more preferably 3 to 30 hours.

Where, when hydration of acrylonitrile is performed by the batch reaction or the semi batch reaction, "reaction temperature" means the temperature either low one (1) hourly average of the reaction mixture temperature from the initiation till the finish of the hydration reaction, or (2) the set temperature of the reaction mixture temperature used when controlling the reaction mixture temperature using the cooling water and such. When hydration of acrylonitrile is performed by the continuous reaction, the "reaction temperature" means the temperature of the reaction mixture in the reactor, and when using the plurality of reactors in the continuous reaction, it means the lowest temperature within the reaction mixture temperature within each reactor.

In other words, when hydration of acrylonitrile is performed by the batch reaction or the semi batch reaction, the "reaction temperature" of the present invention means the lower temperature of either (1) hourly average of liquid temperature of the reaction mixture within the reactor, or (2) the set temperature of the reactor.

At least one type of water-soluble monocarboxylate with carbon number of 2 or more can be added in the raw material water or the reaction mixture (including reaction raw materials and acrylamide produced). In the present invention, the raw material water including at least one type of water-soluble monocarboxylate with carbon number of 2 or more can be supplied to the reactor. When reaction is performed continuously using the plurality of reactors, after adding at least one type of water-soluble monocarboxylate with carbon number of 2 or more to the reaction solution including acrylamide extracted from the reactor, it can be supplied to the next reactor. By this, stability of acrylamide in the reaction solution increases.

The water-soluble monocarboxylate can either be saturated monocarboxylate or unsaturated monocarboxylate. Examples of the saturated carboxylic acid include acetic acid, propionic acid, and n-caproic acid. Examples of unsaturated carboxylic acid include acrylic acid, methacrylic acid, and vinyl acetic acid. Typical examples of salt are sodium salt, potassic salt, and ammonium salt of the saturated carboxylic acid or the unsaturated carboxylic acid.

The additive amount of the water-soluble monocarboxylate is preferably 20 to 5000 mg/kg as acid relative to acrylamide.

Acrylamide produced in the above method is preferably used as aqueous solution having acrylamide concentration of 25 to 60 mass % relative to the total mass of the reaction mixture including acrylamide.

When acrylamide concentration relative to the total mass of the reaction mixture including acrylamide is higher than 60 mass %, since crystal of acrylamide becomes easy to be formed at near room temperature, a heating device is necessary. As a result, not only facility cost increases, but operability such as temperature management becomes complicated. Therefore, although acrylamide concentration of acrylamide aqueous solution is not particularly limited as long as it is in a range so that crystal of acrylamide does not deposit even near room temperature, it is preferably 60 mass % or less, more preferably 55 mass % or less, and most preferably 50 mass % or less.

On the other hand, when acrylamide concentration relative to the total mass of the reaction mixture including acrylamide is 25 mass % or less, tank volume used for preservation or storing becomes excessive, or transportation cost increases. As a result, it becomes disadvantageous in the economical aspect in industrial use. Therefore, acrylamide concentration of acrylamide aqueous solution is preferably 25 mass or more, more preferably 35 mass % or more, and most preferably 40 mass % or more. That is, when acrylamide concentration relative to the total mass of the reaction mixture including acrylamide is 25 to 60 mass %, it is preferable for crystal of acrylamide does not form, and is advantageous in the economical aspect in industrial use.

EXAMPLES

Below, the present invention is explained in detail with examples, although the present invention is not limited to the examples.

Furthermore, in each example below, "%", "ppm" each refers to "mass %" and "mass ppm" unless there is no particular limitation. Room temperature refers to 20° C.

pH is the value at 20° C. which was measured by a glass electrode method.

Example 1

(Preparation of biocatalyst)
*Rodococcus rhodochrous* J1 having nitrile hydratase activity (Accession number: FERM BP-1478; internationally deposited to International Patent Organism Depositary, National Institute of Advanced Industrial Science and Technology (Chuo 6, Higashi 1-1-1, Tsukuba-shi, Ibaraki) on Sep. 18, 1987) was aerobically cultured in a medium containing 2% glucose, 1% urea, 0.5% peptone, 0.3% yeast extract and 0.05% cobalt chloride (pH 7.0) at 30° C. Using a centrifuge and 50 mM phosphate buffer (pH 7.0), the obtained culture was subjected to harvest and washing, thereby preparing a bacterial cell suspension as a biocatalyst (dried cell 15 mass %).

(Reaction from Arylonitrile to Acrylamide)
497 g of 50 mM phosphate buffer (pH 7) cooled to 3° C., and 1.5 g of bacterial cell suspension stored at 5° C. were put in a reactor with a jacket (inner diameter of 10 cm) with an inner volume of 1L.

Next, acrylonitrile at room temperature was supplied to the reactor at 50 g/hr and reaction was initiated. During the reaction, cooling water of 15° C. was flowed in the jacked so that the reaction temperature becomes 25° C.

From the moment where 40 minutes have passed after the reaction was initiated, the reaction temperature was stably controlled at 25° C. During the period until it was stably controlled, the reaction temperature temporarily rose to a maximum of 26° C.

After 6 hours from the initiation of the reaction, supplying of acrylonitrile was stopped, and the reaction was continued.

After 9 hours from the initiation of the reaction, the reaction solution was measured by means of gas chromatography (column: PoraPak-PS (manufactured by Waters), 1 m, 180° C., carrier gas: nitrogen, detector: FID). As a result, acrylamide was only detected at a concentration of 50.1%, and unreacted acrylonitrile was not detected.

Example 2

The reaction was performed in in the same manner as Example 1, except that 50 mM phosphate buffer (pH 7) cooled to 10° C. was put in the reactor, the reaction temperature was set at 15° C., and the temperature of the cooling water of the jacket was set at 5° C.

From the moment where 45 minutes have passed after the reaction was initiated, the reaction temperature was stably controlled at 15° C. During the period until it was stably controlled, the reaction temperature temporarily rose to a maximum of 27.5° C.

After 6 hours from the initiation of the reaction, supplying of acrylonitrile was stopped, and the reaction was continued.

After 12 hours from the initiation of the reaction, the reaction solution was measured by means of gas chromatography (column: PoraPak-PS (manufactured by Waters), 1 m, 180° C., carrier gas: nitrogen, detector: FID). As a result, acrylamide was detected at a concentration of 50.1%, and unreacted acrylonitrile was detected at a concentration of 20 ppm.

Comparative Example 1

The reaction was performed in in the same manner as Example 2, except that 50 mM phosphate buffer (pH 7) cooled to 15° C. was put in the reactor.

From the moment where 50 minutes have passed after the reaction was initiated, the reaction temperature was stably controlled at 15° C. During the period until it was stably controlled, the reaction temperature rose to a maximum of 34° C.

After 6 hours from the initiation of the reaction, supplying of acrylonitrile was stopped, and the reaction was continued.

After 12 hours from the initiation of the reaction, the reaction solution was measured by means of gas chromatography (column: PoraPak-PS (manufactured by Waters), 1 m, 180° C., carrier gas: nitrogen, detector: FID). As a result, acrylamide was detected at a concentration of 49.6%, and unreacted acrylonitrile was detected at a concentration of 4000 ppm.

Example 3

Seven reactors having a jacket (inner diameter of 10 cm) and an inner volume of 1L were connected in series. 50 mM phosphate buffer (pH 7) cooled to 3° C. was continuously-supplied to the first reactor at 780 mL/hr. Further, acrylonitrile at room temperature was continuously-supplied to the first reactor at 214 mL/hr, and bacterial cell suspension stored at 5° C. at 2.0 g/hr. was continuously added to the first reactor. Furthermore, acrylonitrile was supplied to the second reactor at 182 mL/hr. Acrylonitrile was supplied to the third reactor at 133 mL/hr. Moreover, acrylonitrile was supplied to the fourth reactor at 55 mL/hr., and each reactor was stirred. The reaction temperature was controlled using the cooling water (15° C.) of the jacket so that each solution temperature from the first reactor to the seventh reactor becomes 25, 25, 26, 26, 27, 28, and 28° C.

After one day from the initiation of the reaction, the reaction temperatures in the first reactor to the seventh reactor were controlled to their preset temperatures. The reaction solution flowing out from the seventh tank was measured by means of gas chromatography (column: PoraPak-PS (manufactured by Waters), 1 m, 180° C., carrier gas: nitrogen, detector: FID), acrylamide was detected at a concentration of 50.1%, and unreacted acrylonitrile was not detected.

Example 4

The reaction was performed in the same manner as Example 3, except that 50 mM phosphate buffer (pH 7) cooled to 15° C. was continuously supplied at 780 mL/hr to the first reactor, and the reaction temperature was controlled using the cooling water (12° C.) of the jacket so that each solution temperature from the first reactor to the seventh reactor becomes 20, 20, 21, 21, 22, 22, and 23° C.

After one day from the initiation of the reaction, the reaction temperature in the first reactor became 20.7° C. Each reaction temperature from the second reactor to the seventh reactor was controlled to their preset temperatures. The reaction solution flowing out from the seventh reactor was measured by means of gas chromatography (column: PoraPak-PS (manufactured by Waters), 1 m, 180° C., carrier gas: nitrogen, detector: FID), acrylamide was detected at a concentration of 50.1%, and unreacted acrylonitrile was detected at a concentration of 90 ppm.

Example 5

The reaction was performed in the same manner as Example 4, except that acrylonitrile cooled to 15° C. was supplied from the first reactor to the fourth tank.

After one day from the initiation of the reaction, the reaction temperatures from the first reactor to the seventh reactor were controlled to their preset temperatures. The reaction solution flowing out from the seventh reactor was measured by means of gas chromatography (column: PoraPak-PS (manufactured by Waters), 1 m, 180° C., carrier gas: nitrogen, detector: FID), acrylamide was detected at a concentration of 50.1%, and unreacted acrylonitrile was not detected.

Comparative Example 2

The reaction was performed in the same manner as Example 4, except that 50 mM phosphate buffer (pH 7) cooled to 20° C. was continuously supplied at 780 mL/hr. to the first reactor.

After one day from the initiation of the reaction, each reaction temperature from the first reactor to the third reactor became 23.4° C., 22.5° C., and 21.6° C. Each reaction temperature from the fourth reactor to the seventh reactor was controlled to their preset temperatures. The reaction solution flowing out from the seventh reactor was measured by means of gas chromatography (column: PoraPak-PS (manufactured by Waters), 1 m, 180° C., carrier gas: nitrogen, detector: FID), acrylamide was detected at a concentration of 49.9%, and unreacted acrylonitrile was detected at a concentration of 1200 ppm.

TABLE 1

| | Reaction Form | Reaction Temperature [° C.] | Raw Material Water Temperature [° C.] | Acrylonitrile Temperature [° C.] | Reaction Temperature-Raw Material Water Temperature [° C.] | Heat Removal | Unreacted Acrylonitrile [ppm] |
|---|---|---|---|---|---|---|---|
| Example 1 | Semibatch | 25 | 3 | Room Temperature | 22 | Good | 0 |
| Example 2 | Semibatch | 15 | 10 | Room Temperature | 5 | Good | 20 |
| Comparative Example 1 | Semibatch | 15 | 15 | Room Temperature | 0 | Insufficient | 4000 |
| Example 3 | Continuous | 25 | 3 | Room Temperature | 22 | Good | 0 |
| Example 4 | Continuous | 20 | 15 | Room Temperature | 5 | Good | 90 |
| Example 5 | Continuous | 20 | 15 | 15 | 5 | Good | 0 |
| Comparative Example 2 | Continuous | 20 | 20 | Room Temperature | 0 | Insufficient | 1200 |

As shown in the results of Examples 1 to 2 and Comparative example 1, in the case of the semi batch reaction, the temperature of the reaction solution tends to rise immediately after the initiation of the reaction. However, by setting the temperature of the raw material water fed to the reactor to a temperature equal to or more than freezing point and lower than the reaction temperature by 5° C. or more, the reaction heat was well removed without excessively lowering the temperature of the cooling water, or using the reactor having a complicated structure. Therefore, the energy cost and apparatus cost required for cooling of the cooling water were reduced compared to in the past. Also, unreacted acrylonitrile was few, and conversion ratio to acrylamide was high.

Further, as shown in the results of Examples 3 to 5 and Comparative example 2, in the case of the continuous reaction where the plurality of reactor was used, the temperature of the reaction solution tends to rise in the reactor in the upstream side, but by setting the temperature of the raw material water supplied to the reactor to a temperature equal to or more than freezing point and lower than the reaction temperature by 5°

C. or more, the reaction heat was well removed without excessively lowering the temperature of the cooling water, or using the reactor having a complicated structure. Therefore, the energy cost and apparatus cost required for cooling of the cooling water were reduced compared to in the related art. Also, unreacted acrylonitrile was few, and conversion ratio to acrylamide was high.

In Table 1, the reaction temperature in Examples 3 to 5 and Comparative example 2 is a temperature of the first reactor.

Industrial Applicability

According to the method of producing acrylamide of the present invention, the reaction heat at the time of producing acrylamide by hydrating acrylonitrile using the biocatalyst can effectively be removed. Further, conversion ratio from acrylonitrile to acrylamide can be increased. Therefore, the present invention can be produced acrylamide at low cost and with high productivity.

The invention claimed is:

1. A method for producing acrylamide, comprising:
   (a) supplying a raw material water for hydrating acrylonitrile to a reactor,
   (b) supplying acrylonitrile to the reactor, and
   (c) hydrating acrylonitrile with a biocatalyst and said raw material water,
   wherein a temperature of the raw material water for hydrating acrylonitrile in (a) is equal to or more than a freezing point of the raw material water and lower than a reaction temperature by 5° C. or more.

2. The method according to claim 1,
   wherein a temperature of acrylonitrile in in (b) is equal to or more than the freezing point of the raw material water and lower than the reaction temperature by 5° C. or more.

3. The method according to claim 1,
   wherein the hydrating acrylonitrile with the biocatalyst is performed by a semi batch reaction or a continuous reaction.

4. The method according to claim 3, wherein the hydrating acrylonitrile with the biocatalyst is performed by a semi batch reaction.

5. The method according to claim 3, wherein the hydrating acrylonitrile with the biocatalyst is performed by a continuous reaction.

6. The method according to claim 1, further comprising:
   (a') adjusting a temperature of said raw material water for hydrating acrylonitrile to be equal to or more than a freezing point and lower than said reaction temperature by 5° C. or more before (a).

7. The method according to claim 1, wherein (b) is performed after (a) and (c) is performed after (b).

8. The method according to claim 1, wherein said raw material water for hydrating acrylonitrile is at least one selected from the group consisting of water, an aqueous solution of acid and an aqueous solution of an acid salt.

9. The method according to claim 1, wherein said raw material water for hydrating acrylonitrile is an aqueous solution of at least one acid selected from the group consisting of phosphoric acid, acetic acid, citric acid, boric acid, acrylic acid and formic acid.

10. The method according to claim 1, wherein said raw material water for hydrating acrylonitrile is an aqueous solution of at least one acid salt selected from the group consisting of sodium, potassium and ammonium.

11. The method according to claim 1, wherein said raw material water for hydrating acrylonitrile has a pH of 5 to 9.

12. The method according to claim 1, wherein said temperature of said raw material water for hydrating acrylonitrile is lower than a reaction temperature by 10° C. or more.

13. The method according to claim 1, wherein said temperature of said raw material water for hydrating acrylonitrile is lower than a reaction temperature by 20° C. or more.

* * * * *